United States Patent [19]
de la Fonteijne

[11] Patent Number: 4,702,249

[45] Date of Patent: Oct. 27, 1987

[54] APPARATUS FOR THE NON-CONTACT DISINTEGRATION OF CONCREMENTS PRESENT IN A BODY

[75] Inventor: Marcel R. de la Fonteijne, Delft, Netherlands

[73] Assignee: B.V. Optische Industrie "De Oude Delft", Netherlands

[21] Appl. No.: 700,728

[22] Filed: Feb. 12, 1985

[30] Foreign Application Priority Data

Feb. 16, 1984 [NL] Netherlands ........................ 8400504

[51] Int. Cl.$^4$ ............................................. A61B 17/22

[52] U.S. Cl. .................................................. 128/328

[58] Field of Search ...................... 128/328, 24 A, 660; 367/150, 151; 181/400

[56] References Cited

U.S. PATENT DOCUMENTS

| | | | |
|---|---|---|---|
| 3,942,531 | 3/1976 | Hoff et al. | 128/328 |
| 4,311,147 | 1/1982 | Häusler | 128/328 |
| 4,570,634 | 2/1986 | Wess | 128/328 |

FOREIGN PATENT DOCUMENTS

| | | | |
|---|---|---|---|
| 90138 | 10/1983 | European Pat. Off. | 128/328 |
| 2418631 | 10/1975 | Fed. Rep. of Germany | 128/24 A |
| 3146626 | 6/1983 | Fed. Rep. of Germany | 128/24 A |
| 3146627 | 6/1983 | Fed. Rep. of Germany | 128/24 A |

*Primary Examiner*—Leonard E. Smith
*Assistant Examiner*—Paul F. Neils
*Attorney, Agent, or Firm*—Louis E. Marn

[57] ABSTRACT

An apparatus for the non-contact disintegration of concrements present in a body by means of sound shock waves generated by spark discharge between two electrodes in a focus of at least one liquid-filled rotationally symmetrical reflector formed in a reflector block, said sound shock waves being focussed in a focal point situated outside the reflector. Between the focus $F_1$ and the focal point $F_2$, in a region $\beta$ bounded by an imaginary conical surface defined by the edge R of the reflector 2 and the focus $F_1$, there is positioned an object intercepting sound shock waves impinging thereon.

13 Claims, 9 Drawing Figures

APPARATUS FOR THE NON-CONTACT DISINTEGRATION OF CONCREMENTS PRESENT IN A BODY

The present invention relates to an apparatus for the non-contact disintegration of concrements present in a body by means of sound shock waves which are generated by spark discharge in a focus of at least one liquid-filled, rotationally symmetrical reflector formed in a reflector block, said sound shock waves being focussed in a focal point situated outside the reflector.

A similar apparatus is known, e.g. from German Offenlegungsschrift No. 3,146,626.

In this known apparatus the reflector has a semi-ellipsoidal form. The sound shock waves in the known apparatus are generated in the one focus of the ellipsoidal reflector and, insofar as said shock waves actually reach the reflector, are focussed by the reflector in the second focus of the ellipsoid. However, since the reflector should necessarily be open on one side, a considerable portion of the shock waves generated directly leave the reflector cavity without being reflected by the reflector and hence without being focussed in the second focus or focal point.

These shock waves directly emerging from the reflector cavity do not contribute to the disintegration process but do reach the body in which the concrement to be disintegrated is present.

Inherent in the application of the known apparatus, consequently, is an unnecessarily high load on the patient and a relatively low efficiency.

Furthermore, the prior European patent application No. 83 201 074.8 of the present Applicants describes an apparatus of the above described type wherein sound shock waves reflected by a reflector having one focus, as far as originating from the focus, are focussed by a lens in a focal point.

In this prior apparatus, too, a substantial portion of the sound shock waves generated directly leave the reflector. These waves do, at least partly, reach the body via the lens, but are not focussed in the focal point.

It is an object of the present invention to remove the above drawbacks.

To this end according to the invention, an apparatus of the above type is characterized in that between the focus $F_1$ and the focal point $F_2$, in a region bounded by an imaginary conical surface defined by the edge of the reflector and the one focus $F_1$, there is placed an object intercepting sound shock waves impinging thereon.

In a further elaboration of the inventive idea, the intercepting object can be designed so that the intercepted shock waves are yet focussed either directly or indirectly in the focal point, so that the efficiency of the apparatus is improved.

Some embodiments of the apparatus according to the present invention will now be described, by way of example, with reference to the accompanying drawings, in which.

Figure 6:
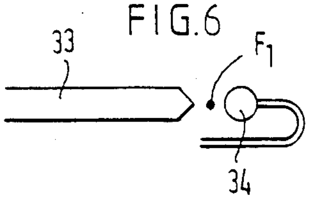
Figure 5:
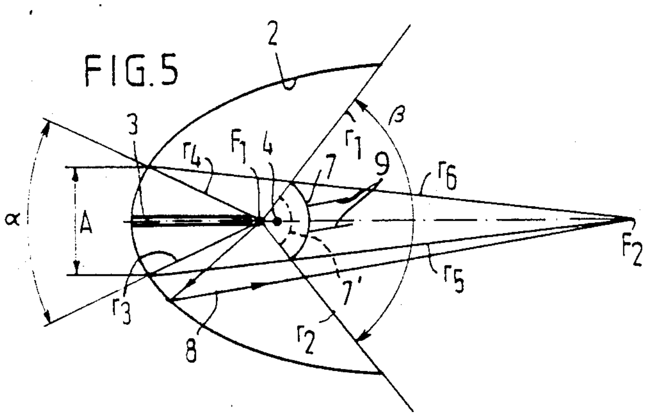
Figure 7:
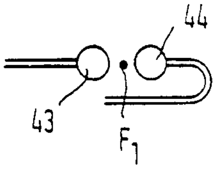
Figure 8:
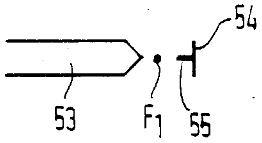
Figure 9:
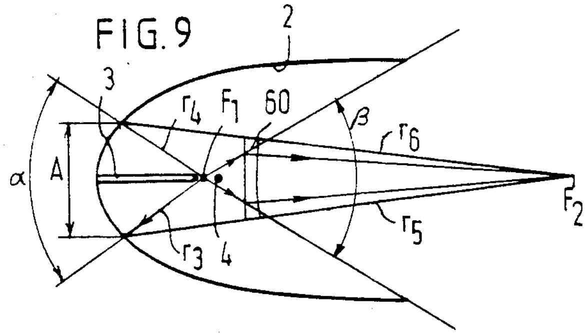
Figure 3:
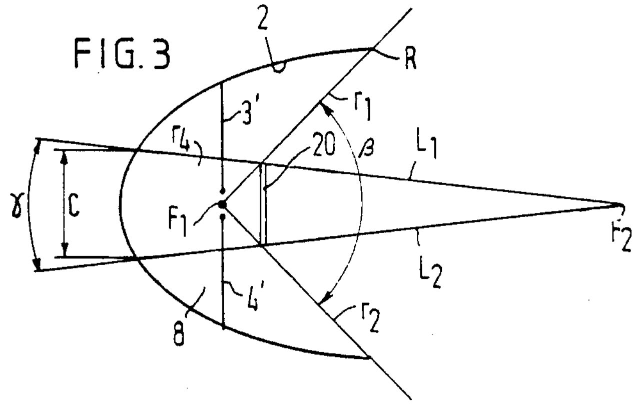
Figure 4:
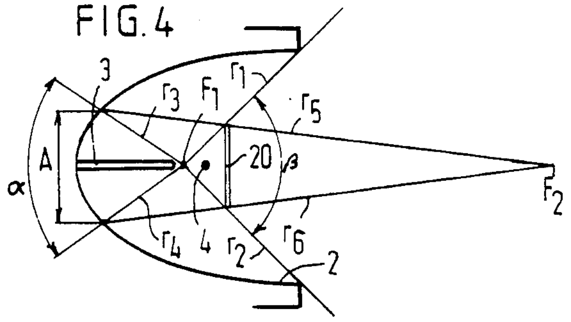

FIG. 3 diagrammatically shows the basic idea of the invention;

FIGS. 4 and 5 illustrate variants of FIG. 3;

FIGS. 6, 7 and 8 show examples of some electrode assemblies according to the invention; and FIG. 9 shows another variant of FIG. 3.

Figure 1:
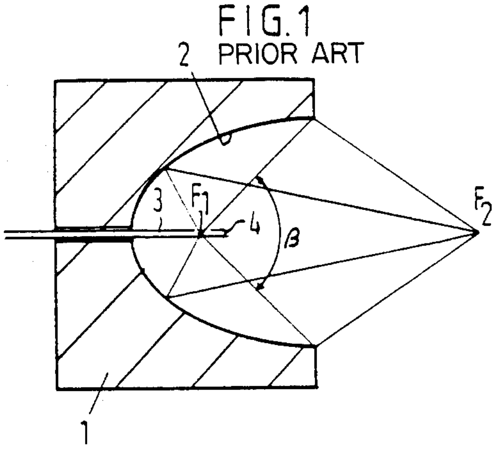
FIG. 1 PRIOR ART
FIG. 1 is a diagrammatical cross-sectional view of a prior art apparatus.

FIG. 1 is a diagrammatical cross-sectional view of a known apparatus for disintegrating concrements present in a body, e.g. renal calculi. The apparatus comprises a reflector block 1 wherein a reflector 2 is formed which has the form of a part of an ellipsoid. Within the reflector lies the one focus $F_1$ of the ellipsoid. Outside the reflector lies the second focus $F_2$. By means of two electrodes 3,4 a spark discharge can be brought about in the focus $F_1$, which—as the reflector cavity is filled with a suitable liquid—results in sound shock waves originating from the focus $F_1$. In this example, the electrodes are situated on the line connecting $F_1$ and $F_2$. Insofar as said sound shock waves are reflected by the reflector 2, they are focussed in the second focus $F_2$. The second focus $F_2$ is therefore sometimes called the focal point. In practice, the reflector cavity may be closed with a membrane which is pressed against a patient's body. If the focal point $F_2$ coincides with a concrement, such concrement can be disintegrated by the shock waves focussed in $F_2$. The reflector, however, may also be placed in a liquid bath.

The figure shows that shock waves having an initial direction lying within the region indicated at $\beta$ cannot impinge upon the reflector and hence cannot be focussed in $F_2$ either. Consequently, such shock waves do not contribute to the disintegration process, but do form a load on the patient.

According to the present invention, these so-called direct shock waves can be prevented from reaching the patient and in a further elaboration of the inventive idea, these direct shock waves can at least partly, be converted into shock waves which do permit being focussed in $F_2$.

Figure 2:
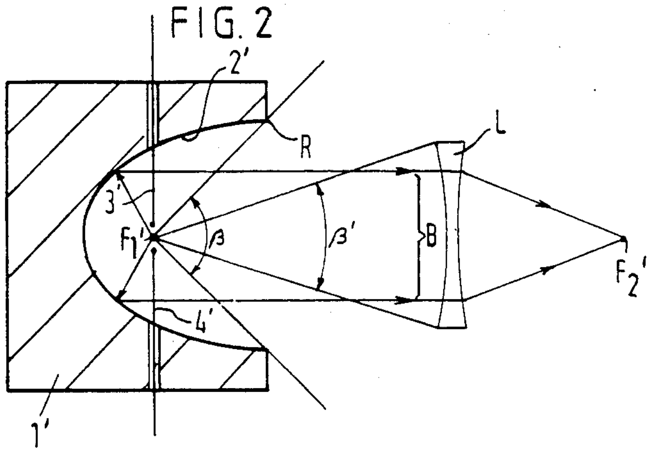
FIG. 2 is a diagrammatical cross-sectional view of another apparatus for disintegrating concrements.

FIG. 2 diagrammatically shows an apparatus for the non-contact disintegration of concrements. This apparatus is of the type as described in the prior European patent application No. 83 201 074.8 and, again, comprises a reflector block 1' wherein a reflector 2' is formed which has a paraboloidal form, with a focus $F_1'$. Although it is possible to employ the same electrode configuration in such a reflector as the one shown in FIG. 1, FIG. 2 shows a different electrode configuration, wherein the electrodes 3', 4' extend approximately transversely to the line connecting $F_1'$ and the focal point $F_2'$. The proximal ends of the electrodes 3' and 4' lie on either side of the focus $F_1'$, so that by energization of the electrodes sound shock waves can be generated that have their origin in $F_1'$. A part of the shock waves thus generated is reflected by the reflector 2'. Since the reflector 2' is parabolic in cross-section, all shock waves originating from the focus $F_1'$ and reflected by the reflector are converted into a parallel beam B, which is focussed by one or more suitable lenses in a focal point $F_2'$.

This configuration also has a region $\beta$ for which it holds that sound shock waves having an initial direction lying within the confines of the region $\beta$ do not reach the reflector. Such waves do, at least partly, reach the body wherein the concrement to be disintegrated is present, but are not focussed in the focal point $F_2'$.

The same applies if a reflector having a different form, e.g. spherical, is employed, with an adapted system of lenses. In that case as well there is such a region $\beta$.

FIG. 3 diagrammatically shows the basic idea of the present invention. Again, there is shown a reflector which may have a form as shown in FIGS. 1 or 2, or yet another form, and which in the last two cases coacts with one or more lenses adapted to focus the shock waves reflected by the reflector in a focal point $F_2$.

FIG. 3 again shows the focus of the reflector at $F_1$ and shows an electrode configuration as depicted in FIG. 2. Furthermore, the region $\beta$ is indicated again. This region $\beta$ is bounded by edge rays connecting the focus $F_1$ to the edge R of the reflector and extending beyond the edge R, too. It is observed that with a short reflector the object may lie outside the reflector and the apex angle of the region $\beta$ may be 180° or even obtuse. Said edge rays form a conical surface two edge rays of which, indicated at $r_1$, $r_2$, lie in the plane of drawing.

As noted hereinbefore, shock waves having an initial direction of propagation lying within the region $\beta$ not contribute to the disintegration process. These shock waves do constitute a load on the patient.

According to the present invention, these so-called direct shock waves are prevented from reaching the patient by placing an object intercepting the direct shock waves in the region $\beta$. Such an object is indicated at 20 in FIG. 3. The outer edge of object 20 preferably coincides with the edge rays of the region $\beta$. In fact, if the object should extend beyond the region $\beta$, shock waves contributing to the disintegration process would be intercepted as well.

In certain situations the outer edge of the object 20 may fall within the edge rays of the region $\beta$. This is the case, for example, in the configuration shown in FIG. 2, wherein a conical region $\beta'$ can be defined that is formed by edge rays connecting the focus $F_1'$ to the peripheral edge of the lens system L. If the apex angle of the conical region $\beta'$ is smaller than that of the conical region $\beta$, i.e. if the lens system L is spaced apart from the reflector, direct shock waves occurring in the region located within region $\beta$ but without region $\beta'$ will not reach the lens system directly. If absorbing material is present between the edge R of the reflector and the lens system L, such shock waves will be absorbed and will not reach the patient. In that case an object 20 whose outer edge coincides with the edge rays of the region $\beta'$ will suffice.

Similar considerations apply if, in operation, there is some interspace between the edge of an elliptical reflector and the patient.

It is important for the intercepting object to be as small as possible, as the object is associated with a shadow region $\beta$. Shock waves impinging on the reflector within said shadow region $\beta$ intercepted, after reflection, by the object and, although said shock waves have the proper direction for being focussed in the focal point $F_2$, they do not contribute to the disintegration process. As a result, the efficiency of the apparatus diminishes, somewhat, which, however, can be overcome by generating shock waves of higher energy. This is possible because the load on the patient has been considerably reduced by the interception of the direct shock waves.

The shadow region $\gamma$ is indicated in FIG. 3 for an elliptical reflector. This region is defined by a conical surface consisting of generatrices, two of which, $L_1$ and $L_2$, are visible, and which meet in the focal point $F_2$, the circumference of the intercepting object defining a section of the conical surface. The section of the conical surface intercepted by the reflector is indicated at C.

In case the reflector is a parabolic reflector coacting with a lens system, the region $\gamma$ defined by a cylindrical surface whose generatrices are parallel to the line connecting $F_1$ and $F_2$, with the circumference of the intercepting object defining a section of the cylindrical surface. The section C in that case is smaller than that shown in FIG. 3.

It is noted that in all cases the section C is smaller as the intercepting object within the confines of the conical region $\beta$ (or $\beta'$) is closer to the focus $F_1$.

When the intercepting object is very close to $F_1$, the section C is very small and, consequently, the loss of efficiency is also very small, while yet the patient is not subjected to shock waves that do not contribute to the disintegration process.

The loss of efficiency due to the shadow region $\gamma$ can be prevented by using an electrode configuration extending along the line connecting $F_1$ and $F_2$, as shown in FIG. 1. This will be explained hereinafter.

FIG. 4 again shows a reflector 2, which may be of the elliptical type, but may have another form. The one electrode 3 is shown on a larger scale for clarity and of the other electrode 4, only the end lying between $F_1$ and $F_2$ is shown.

As a result of the finite dimensions of the electrode 3, there is produced a conical shadow region $\alpha$. A indicates the section of the shadow region by the reflector. Within this region, no shock waves can reach the reflector. The shadow region is bounded by a conical surface, two generatrices $r_3$, $r_4$ of which lie in the plane of drawing.

In the case of an elliptical reflector, shock waves reaching the reflector along the lines or edge rays $r_3$, $r_4$ are focussed in the focal point $F_2$ via edge rays $r_5$, $r_6$. Edge rays $r_5$, $r_6$ extend parallel to the line connecting $F_1$ and $F_2$ if the reflector is a parabolic reflector.

At any rate, no reflected shock waves that can be focussed in $F_2$ can be produced within the region bounded by edge rays $r_5$, $r_6$, due to the finite dimensions of electrode 3. An object placed in such a region between $F_1$ and $F_2$, consequently, does not affect the efficiency of the apparatus. An object 20 thus positioned, which prevents direct shock waves from emanating from the reflector, is shown in FIG. 4. In this situation, the sections A and C (FIG. 3) coincide.

According to a further elaboration of the inventive idea, the intercepting object may be designed so that the direct shock waves intercepted are converted into shock waves that can contribute to the disintegration process. This is possible if the intercepting object is designed as a lens or as a reflector.

In case the intercepting object is designed as a lens, said lens should change the direction of the direct shock waves in such a manner that the direct shock waves are focussed in the focal point $F_2$ either directly (elliptical reflector), or via the lens system L (parabolic or other type of reflector).

An example of the use of such a lens is shown diagrammatically in FIG. 9 for an elliptical reflector and an electrode configuration as shown in FIG. 1.

FIG. 9 again shows the region $\beta$ and the intercepting object, here designed as lens 60, is present within the region $\beta$ (or $\beta'$). Since reflector 2 in this embodiment is an elliptical reflector focussing the reflected shock waves originating from the focus $F_1$ in the focal point $F_2$ directly, without the intermediary of a lens system L, lens 60 is designed so that it focusses shock waves originating from focus $F_1$ directly in focal point $F_2$.

Since lens 60 converts all direct shock waves impinging thereon into shock waves that contribute to the disintegration process, the lens may extend beyond region $\beta$, if desired.

As a result of the electrode configuration shown, however, there is produced a conical shadow region $\beta$ bounded by edge rays $r_3$, $r_4$. This is a result of the finite dimensions of electrode 3. Lens 60 should not extend beyond a conical surface extending between focal point $F_2$ and the circumferential edge of the section A of the region $\alpha$ by the reflector. This conical surface is indicated in the figure by edge rays $r_5$, $r_6$. If in fact the lens should extend beyond this conical surface, shock waves reflected by the reflector and already focussed in the focal point $F_2$, would also be intercepted by the lens: such shock waves would therefore not reach $F_2$.

In case the reflector is a parabolic reflector, lens 60 should accordingly not extend beyond a cylindrical surface formed by generatrices starting from the circumference of the section A, and extending parallel to the line connecting $F_1$ and $F_2$. To differently formed reflectors coacting with a lens system L similar considerations apply.

It is noted that electrode 4, being located between focus $F_1$ and the lens, produces a shadow region on the lens. This shadow region should naturally be smaller than the lens. This can be realized in practice in a simple manner by placing the lens relatively close to the focus $F_1$, as shown in the figure.

It is further observed that if an electrode configuration is employed as shown in FIG. 2, the electrodes do not form shadow regions on the lens 60, and opposite the lens 60 on the reflector. In that case, as stated before regarding the intercepting object 20, the lens should be made as small as possible, but should at least cover the region $\beta$ (or $\beta'$).

As already mentioned, the intercepting object may be designed as a reflector. Such a configuration is shown in FIG. 5.

FIG. 5 again shows an ellipsoidal reflector 2 and the one electrode 3 of an electrode system as shown in FIG. 1. The edge rays emanating from focus $F_1$ bounding the region $\beta$ are again indicated at $r_1$, $r_2$.

Furthermore, a region $\alpha$ is indicated that is bounded by edge rays $r_3$, $r_4$. No shock waves can reach the reflector within the region $\alpha$ as a result of the finite dimensions of electrode 3, and shock waves propagating along the edge rays $r_3$, $r_4$ are again focussed in focal point $F_2$ via edge rays $r_5$, $r_6$. Within the region $\beta$ and within the conical region defined by edge rays $r_5$, $r_6$, there is positioned a reflector 7 reflecting incident direct shock waves in such a manner that these reach reflector 2 at least partly via focus $F_1$ and consequently, are still focussed in the second focal point $F_2$. This can be effected by designing reflector 7 as a concave spherical mirror whose concave side faces focus $F_1$.

A shock wave thus reflected and subsequently focussed onto $F_2$ is indicated at 8.

Naturally, the use of a reflector 7 is only useful if the solid angle enclosed by such reflector is larger than the solid angle enclosed by rays $r_3$, $r_4$.

This can be realized in practice without any problems and may lead to an improvement in efficiency in the order of 20%.

It is observed that FIG. 5 shows the reflector 7 with the maximum dimensions tolerable to prevent the interception of shock waves focussed normally by the ellipsoidal reflector onto the focal point $F_2$.

However, reflector 7 may be positioned closer to focus $F_1$ if correspondingly smaller dimensions are chosen, as indicated in FIG. 5 by a broken line 7'.

The shock waves reflected via reflector 7 and subsequently via the ellipsoidal reflector 2 reach the focal point $F_2$ later than do the shock waves reflected by the ellipsoidal reflector only. This need not be a drawback in itself. However, it is possible to choose the dimensions of the apparatus and the time between the spark discharges in such a manner that the two types of shock waves interfere with one another in a positive manner, i.e. amplify one another in the second focal point $F_2$.

Thus, for example, reflector 7 can be suspended from the reflector block by means of thin metal strips, not shown.

Such a reflector, as is the case with the lens 60, may be used similarly with a differently formed reflector 2 and with a different electrode configuration.

In a further embodiment of the inventive idea, reflector 7 is designed in full or in part as a transducer connected to leads 9 for converting shock waves received into electric signals. Such a transducer can be used in orientating the ellipsoidal reflector. In that case, it is not necessary, as customary, to use X-rays for the orientation. This is better for the patient and also makes for more accurate orientation, as the same type of waves is used then as for the disintegration.

Between electrodes 3 and 4, a spark discharge with a relatively small energy content is brought about and by means of the transducer the energy reflected through the tissue present at the focal point $F_2$ is measured. The reflected energy is maximal when the focal point $F_2$ coincides with a concrement. As soon as the concrement has thus been located, the energy content of the spark discharge is increased so as to disintegrate the concrement.

Orientation can also be performed entirely by means of the transducer, if this is first energized as a transmitter and subsequently is used as a receiver. Furthermore, the transducer can be used to monitor the quantity of energy transmitted and to check whether the concrement has already been disintegrated.

Reflector 7 may be positioned very close to the first focus $F_1$, which makes it possible to position reflector 7 at the place of electrode 4 and to combine it with electrode 4.

Although electrode 4 is not situated exactly in focus $F_1$, the distance between electrodes 3 and 4 may be chosen so small that for practical purposes, electrode 4 and also electrode 3 can be deemed to be situated in focus $F_1$.

Some embodiments of electrode assemblies thus designed are shown diagrammatically in FIGS. 6, 7 and 8, respectively showing electrode assemblies 33, 34; 43, 44 and 53, 54, with electrodes 33, 43, 53 each being comparable to electrode 3 of FIGS. 1, 4, 5 and 9, and electrodes 34, 44, 54 each being comparable with electrode 4 of these figures.

In the embodiments shown, at least the surfaces of electrode 34, 44, and 54, respectively facing electrode 33, and 43, and 53 are designed so that the shock waves produced by spark discharge are reflected. Since these surfaces are disposed very close to focus $F_1$, their shape is not so important as long as reflection takes place in the direction of the ellipsoidal reflector.

Thus, for instance, the electrodes 34 and 44, respectively shown in FIG. 6 and FIG. 7, are spherical, whereas the reflecting electrode 54 shown in FIG. 8 is plane. In order to concentrate the spark discharge, there may be provided on the electrodes a projection extending in the direction of the opposite electrode, as shown by way of example at 55 in FIG. 8.

It is observed that the shape of the electrode 54 shown in FIG. 8 lends itself very well for said electrode to be designed as a transducer, as described hereinbefore.

Electrodes 33 and 53, respectively shown in FIGS. 6 and 8, are rod-shaped, with a pointed end directed towards electrodes 34 and 54, respectively. Electrode 43 shown in FIG. 7, like electrode 44, is spherical.

According to a further embodiment of the inventive idea, the surface of the respective electrodes 3, 33, 43, and 53, may be reflective, so that the shock waves impinging thereon are reflected to the ellipsoidal reflector. In the embodiment shown in FIG. 5, such reflection may take place both directly and via reflector 7.

In the embodiments shown in FIGS. 3, 4, and 9, too, electrodes having reflecting surfaces may be employed. Electrodes having reflecting surfaces may also be employed in combination with an intercepting object 20, a lens 60 or a reflector 7.

In the situation shown in FIG. 5, at least one of the electrodes 3, 4 has a reflecting surface oriented towards the other electrode.

In that case, the object, the lens or the reflector 7 intercepts the shock waves in the region $\beta$ that propagate outside the shadow region lying behind the electrode 4. If, however, the shadow region of electrode 4 is likewise bounded by the edge rays $r_1$, $r_2$ or is even larger, a additional reflector is useless for obtaining a higher efficiency or a lower load on the patient. In an electrode system as shown in FIGS. 2 or 3, there is naturally no shadow region of an electrode on the intercepting object 20, the lens 60, or the reflector 7, so that in such a case the use of reflecting electrodes in practice will always be attended by the use of an intercepting object 20, a lens 60 or a reflector 7.

Various modifications of the present invention will readily occur to those skilled in the art after reading the foregoing. Such modifications are deemed to fall within the scope of the present invention.

I claim:

1. An apparatus for the non-contact disintegration of concrements present in a body by means of sound shock waves generated by spark discharge between two electrodes in a focus $F_1$ of at least one liquid-filled rotationally symmetrical reflector formed in a reflector block, said sound shock waves being focussed on a focal point $F_2$ situated outside reflector block, characterized in that between said focus $F_1$ and said focal point $F_2$, in a region bounded by an imaginary conical surface defined by an edge of said reflector and said focus $F_1$, there is positioned a lens permitting passage of sound shock waves originating from said focus $F_1$ and to focus said sound shock waves to said focal point $F_2$.

2. The apparatus as defined in claim 1 wherein said electrodes are positioned on either side of said focus $F_1$ on a straight line extending through said focus $F_1$ and said focal point $F_2$ and said lens is positioned in a region defined by a section of said reflector by locus of lines extending from said focus $F_1$ tangent to an electrode situated between said focus $F_1$ and said reflector and by lines drawn from points of a circumferential line of said region in a direction of reflection sound shock waves originating from said focus $F_1$ reflected in points of said circumferential line of said region and focussed in the focal point $F_2$.

3. An apparatus for the non-contact disintegration of concrements present in a body by means of sound shock waves generated by spark discharge between two electrodes in a focus $F_1$ of at least one liquid-filled rotationally symmetrical reflector formed in a reflector block, said sound shock waves being focussed on a focal point $F_2$ situated outside said reflector block, characterized in that between said focus $F_1$ and said focal point $F_2$, in a region bounded by an imaginary conical surface defined by an edge of said reflector and said focus $F_1$, there is positioned a reflecting surface facing said reflector and having a form to reflect against said reflector sound shock waves originating from said focus $F_1$ and impinging on said reflecting surface.

4. The apparatus as defined in claim 3 wherein said electrodes are positioned on either side of said focus $F_1$ on a straight line extending through said focus $F_1$ and said focal point $F_2$ and said reflecting surface is positioned in a region defined by a section of said reflector by a locus of lines extending from said focus $F_1$ tangent to an electrode situated between said focus $F_1$ and said reflector and by lines drawn from points of a circumferential line of said region in a direction of reflection of sound shock waver originating from said focus $F_1$ reflected in points of said circumferential line of said region and reflected via the focus $F_1$ to said reflector.

5. The apparatus as defined in claims 2 or 4 wherein at least one of said electrodes is formed of a reflecting surface facing said other electrode.

6. The apparatus as defined in claims 1 or 3 wherein one electrode of said two electrodes includes a reflecting surface facing said other electrode.

7. An apparatus for the non-contact disintegration of concrements present in a body by means fo sound shock waves generated by spark discharge between two electrodes in a focus $F_1$ of at least one liquid-filled rotationally symmetrical reflector formed in a reflector block and focussed on a focal point $F_2$ situated outside said reflector block and wherein said electrodes are situated on either side of said focus $F_1$ on a straight line extending through said focus $F_1$ and said focal point $F_2$, characterized in that said electrode situated between said focus $F_1$ and said focal point $F_2$ is formed with a reflecting surface facing said other electrode, said electrode situated between said focus $F_1$ and said focal point $F_2$ being spherical.

8. The apparatus as defined in claim 7 wherein said electrode disposed between said reflector and said focus $F_1$ is formed with a reflecting surface facing said electrode situated between said focus $F_1$ and said focal point $F_2$.

9. The apparatus as defined in claim 8 wherein said electrode disposed between said reflector said focus $F_1$ is formed with a conical reflecting surface having an apex which faces said electrode situated between said focus $F_1$ and said focal point $F_2$.

10. An apparatus for the non-contact disintegration of concrements present in a body by means of sound shock waves generated by spark discharge between two electrodes in a focus $F_1$ of at least one liquid-filled rotationally symmetrical reflector formed in a reflector block and focussed on a focal point $F_2$ situated outside said reflector block and wherein said electrodes are situated on either side of said focus $F_1$ on a straight line extending through said focus $F_1$ and said focal point $F_2$, said electrode situated between said focus $F_1$ and said focal point $F_2$ having a substantially planar reflecting surface extending transversely to a line connecting said focus $F_1$ and said focal point $F_2$.

11. The apparatus as defined in claim 10, wherein a projection is provided centrally on said reflecting surface of said electrode.

12. An apparatus for the non-contact disintegration of concrements present in a body by means of sound shock waves generated by spark discharge between two electrodes in a focus $F_1$ of at least one liquid-filled rotationally symmetrical reflector formed in a reflector block, said sound shock waves being focussed on a focal point $F_2$ situated outside reflector block, characterized in that between said focus $F_1$ and said focal point $F_2$, in a region bounded by an imaginary conical surface defined by an edge of said reflector and said focus $F_1$, there is positioned a transducer which when energized transmits sound waves.

13. The apparatus as defined in claim 12 wherein said transducer is adapted to convert impinging sound waves into an electric signal.

* * * * *